US005330532A

United States Patent [19]

Ranawat

[11] Patent Number: 5,330,532
[45] Date of Patent: Jul. 19, 1994

[54] KNEE JOINT PROSTHESIS

[76] Inventor: Chitranjan Ranawat, 535 E. 70th St., New York, N.Y. 10021

[21] Appl. No.: 612,605
[22] Filed: Nov. 9, 1990
[51] Int. Cl.⁵ .............................. A61F 2/38
[52] U.S. Cl. ............................................ 623/20
[58] Field of Search ............... 623/20, 16, 18; 606/88

[56] References Cited

U.S. PATENT DOCUMENTS

| | | |
|---|---|---|
| 3,694,821 | 10/1972 | Moritz . |
| 3,715,763 | 2/1973 | Link ..................... 623/20 |
| 3,806,961 | 4/1974 | Müller ................... 623/20 |
| 3,824,630 | 7/1974 | Johnston . |
| 3,840,905 | 10/1974 | Deane . |
| 3,869,731 | 3/1975 | Waugh et al. ......... 623/20 |
| 3,878,566 | 4/1975 | Bechtol ................. 623/20 |
| 3,918,101 | 11/1975 | Lagrange et al. ...... 623/20 |
| 4,136,405 | 1/1979 | Pastrick et al. ........ 623/20 |
| 4,209,861 | 7/1980 | Walker et al. . |
| 4,298,992 | 11/1981 | Burstein et al. . |
| 4,309,778 | 1/1982 | Buechel et al. ........ 623/20 |
| 4,353,135 | 10/1982 | Forte et al. ........... 623/20 |
| 4,470,158 | 9/1984 | Pappas et al. . |
| 4,568,348 | 2/1986 | Johnson et al. . |
| 4,586,933 | 5/1986 | Shoji et al. ........... 623/20 |
| 4,634,444 | 1/1987 | Noiles . |
| 4,650,490 | 3/1987 | Figgie, III . |
| 4,662,889 | 5/1987 | Zichner et al. . |
| 4,770,663 | 9/1988 | Hanslik et al. . |
| 4,790,853 | 12/1988 | Engelbrecht et al. . |
| 4,822,365 | 4/1989 | Walker et al. . |
| 4,822,366 | 4/1989 | Bolesky . |
| 5,011,496 | 4/1991 | Forte et al. ........... 623/20 |

Primary Examiner—David Isabella
Assistant Examiner—Elizabeth M. Burke
Attorney, Agent, or Firm—Rosen, Dainow & Jacobs

[57] ABSTRACT

An improved total knee joint prosthesis having femoral, tibial and patellar components wherein the trochlear groove in the femoral component of the knee joint prosthesis possesses a depth-width ratio that allows the patellar component to sit deeper in the trochlear groove during knee flexion.

3 Claims, 7 Drawing Sheets

KNEE JOINT PROSTHESIS

DESCRIPTION OF THE INVENTION

1. Technical Field

The present invention relates to an improvement in existing total knee joint prosthesis having femoral, tibial and patellar components. The improvement of the present invention is found in the depth to width configuration of the trochlear groove in the femoral component of the knee joint prosthesis.

Knees, the body's largest joints, are subject during waking hours to a variety of stresses. Since the knees bear the body's weight, activities such as walking, running, jumping, kneeling, pivoting, leaning, etc. take their toll over the years. Because the knee is not designed to withstand the rigors that modern life inflicts upon it, it is the most vulnerable and unstable of all of the body's joints.

A common misconception about the manner in which the knee functions is that it operates in a single plane like a hinge. In fact it functions using a variety of motions. When a knee functions within its own limits as to its movements, there is generally no problem. However, if excessive stresses or strains are put on the knee suddenly or over an extended period, major problems can arise.

The knee connects the femur (the thigh bone) with the tibia (the leg bone). The femur and tibia as detailed more specifically hereinafter, are held together by four major ligaments that comprise bands of fibrous, slightly elastic tissue which act as the anatomical equivalent of rubber bands holding the joint in place.

The ends of the femur and tibia, situated one on top of the other, are wrapped in a cartilage gristle-like material that acts as a natural shock absorber and prevents the substantially contiguous condyle ends of the femur and tibia from rubbing against each other.

In front of the knee is the patella or knee cap which helps protect the interfacing femur-tibia area from harm. Although not really designed to do so, the joint structure described above, within reason, allows the knee to swing back and forth in a rocking motion, and also roll, twist and slide.

A number of things can go wrong with the knee. Bones break, ligaments snap, cartilage tears, and the kneecap can slip out of alignment.

When one or more of these knee problems occurs, natural healing and repair may not be possible. In such event a knee joint prosthesis may present a desirable alternative.

The knee prosthesis i.e. the knee joint replacement, used in the present invention has been referred to as a "non-constrained" type as it makes use of some or all of the natural ligaments to control the mode of articulation and/or prevent the separation of the opposing bearing surfaces of the prosthesis.

As discussed above, the knee joint has a variety of movements. It is important to recognize that various movements and an efficient prosthesis should be able to duplicate these movements. Articulation of the natural knee comprises both flexion and rotation modes.

Flexion occurs when the tibia is at full extension, i.e. perpendicular to the ground, and is then moved backward about the knee's joint axis to a maximum at full flexion where the tibia is substantially parallel to the ground.

Rotation occurs when there is arcuate movement along the tibial axis.

The limits to flexion and rotation movements in the natural knee is a function of the femoral and tibial condyles along with the elasticity and length as well as the positioning of the four ligaments generally described above, e.g. the two collateral and two cruciate ligaments, which connect the femur to the tibia.

The natural knee joint also possesses cartilage discs or meniscii intermediate the femur and tibia. These meniscii act as cushions between the condylar ends of the bones that meet in a joint and conform in general to the femoral surfaces and are capable of movement independent of the femoral and tibial condyles.

2. The Prior Art

U.S. Pat. No. 4,298,992 discloses a knee joint prosthesis which does not use a trochlear groove of varying diameters as taught in the instant invention.

U.S. Pat. No. 4,470,158 discloses an alternative knee joint prosthesis which does not possess the trochlear groove design of the present invention.

U.S. Pat. No. 4,650,490 discloses a human knee prothesis wherein the adjusted patellar tendon length to the prosthetic patellar height ranges between 1.2 and 0.9.

SUMMARY OF THE INVENTION

As stated above, the invention relates to a total knee joint prosthesis wherein femoral and tibial components replace the natural femoral and tibial ends that comprise the knee joint when the joint cannot repair itself.

As in the prior art, the femoral component of the instant invention that is attached to the femur comprises a pair of identical laterally spaced-apart femoral condylar bearing portions or tracks each of which is smoothly convexly curved in lateral profile, generally to match the curvature of an anatomical femoral condyle. Each femoral condylar portion is laterally convexly curved along its anteroposterior extent. The anterior portions of the condyles merge smoothly with a concave mid portion that defines a trochlear groove area running parallel to the condyles that receives a patellar prosthesis. The medial part of the trochlear groove area is concave according to a predetermined depth-width ratio. The predetermined depth to width ratio along the axis of the trochlear groove allows the leg to flex with substantially less stress and strain on the ligaments that support the knee joint.

The dome-shaped patellar prosthesis that rides in the trochlear groove can have varying diameters depending upon the size of the patient's natural patella, and is affixed to the modified natural patella and rides in the trochlear groove located between the laterally spaced apart femoral condylar portions. The width of the trochlear groove in which the patella prosthesis rides is determined at any given location along the length of one of the condyles by determining the highest point at the location of the shoulder of either one of the condylar portions and connecting it by the most direct line to the highest point on the shoulder of the diametrically opposite condylar portion. The depth of the groove is determined by measuring the perpendicular distance between the line connecting the high points on the opposite condylar shoulders as described above, to the lowest point of the groove. In general with respect to the arc comprising the trochlear groove of the present invention, as it gets wider, it correspondingly gets deeper. Proceeding from the antero-superior portion of the femoral component along the surface thereof to the inferoposterior portion of the article, the groove gradually gets wider until it reaches a maximum width between the shoulders whereupon the width distances lessen in value.

In using a total knee joint prosthesis, an attempt is made as much as possible to simulate and allow normal lateral angulation and rotation of the prosthetic knee joint.

Over the years, despite the progress made in developments in the "total" and "stabilized" prosthetic knee joints, problems have arisen because the soft tissue is inadequate for one reason or another to provide the required stability, which in turn places considerable strain on the prosthesis with resultant failure by dislodgement of the components.

According to one method of the prior art, implantation of the prosthetic device is made by making a medial parapatellar approach through the knee joint capsule. The proximal portion of the capsular incision extends longitudinally into the quadraceps tendon rather than separating the vastus medialis from the tendinous tissue. The tissues are dissected for a short distance around the tibia and distal femur both medially and laterally and the knee is flexed. The patello-femoral ligament is released to allow easier mobilization of the patella. Osteophytes are removed from the intra condylar notch and the anterior cruciate ligament if present, is excised.

In tight varus knees, a small curved osteotome is directed medially along the proximal tibia to release the meniscotibial ligament and allow anterior subluxation of the tibia.

After removing the scarred synovium and osteophytes the outline of the patella is defined. The articular surface of the patella is removed taking care to make a flat surface. Patellar templates are then used to determine appropriate sizing. The selected template is then placed on the patella is drilled with a patellar drill.

It is an important feature of the present invention to recognize that the quadriceps extensor mechanism comprising the vasti internus and externus, rectus and crureus all join into a common tendon inserted into the patella. Considering how the quadriceps mechanism works in conjunction with the patella in a normal knee joint, it is believed, pursuant to the present invention, that if the patella is allowed to fit deeper into the trochlear groove of the implanted femoral component, there is less stretching involved in the tendons and the muscles thereby resulting in less force across the patella. As a result, the strain in the entire quadriceps system is reduced, i.e., is of lower magnitude and is more evenly distributed.

DETAILED DESCRIPTION OF THE PREFERRED EMBODIMENTS OF THE INVENTION

Because of the intricate construction of the components comprising the present invention, the description of the invention will utilize FIGS. 1 through 9 interchangeably rather than discussing them sequentially in order to have a clear understanding of the invention.

Figure 1:
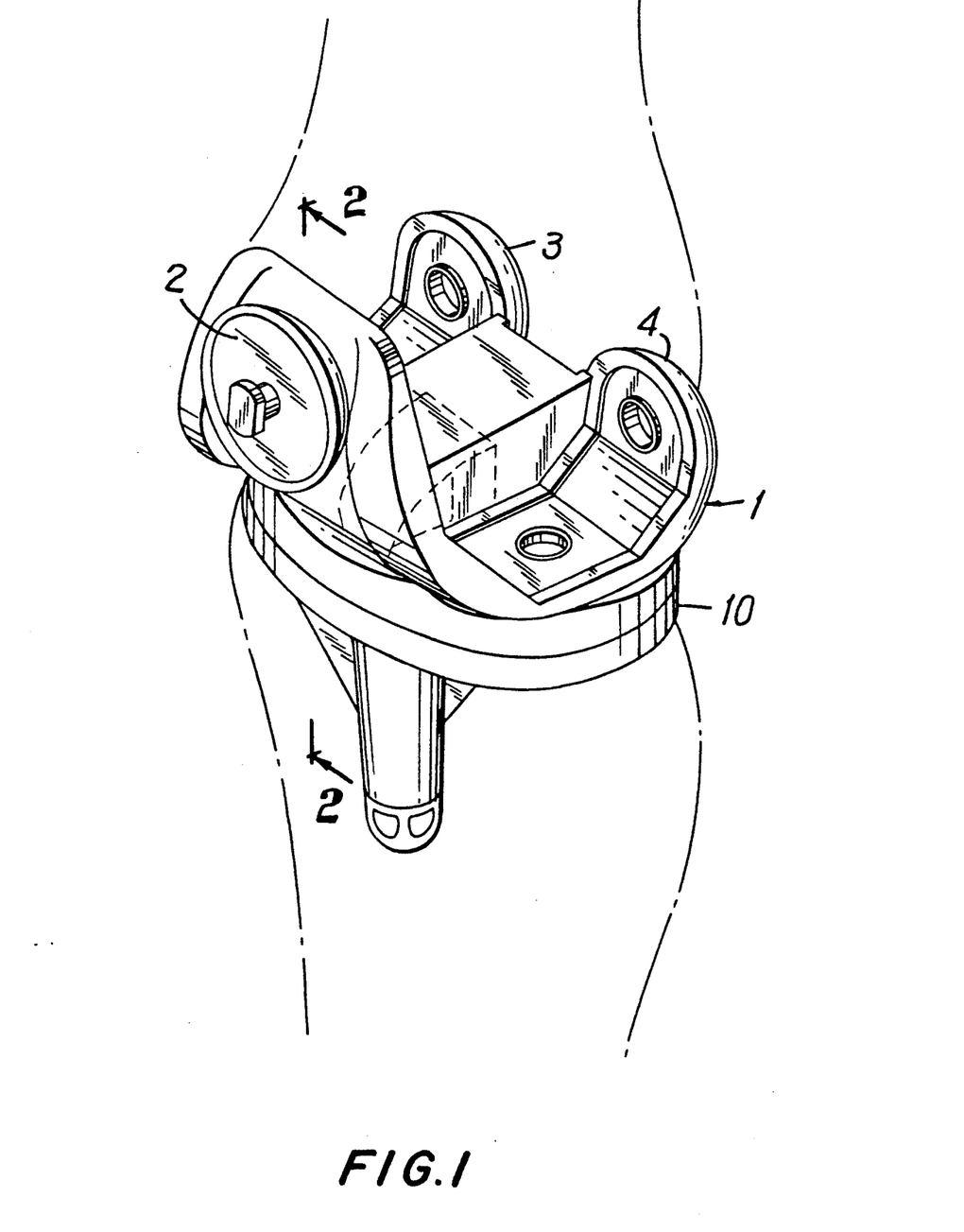
FIG. 1 is a perspective view of an artificial knee joint in accordance with the present invention.
Figures 2, 3:
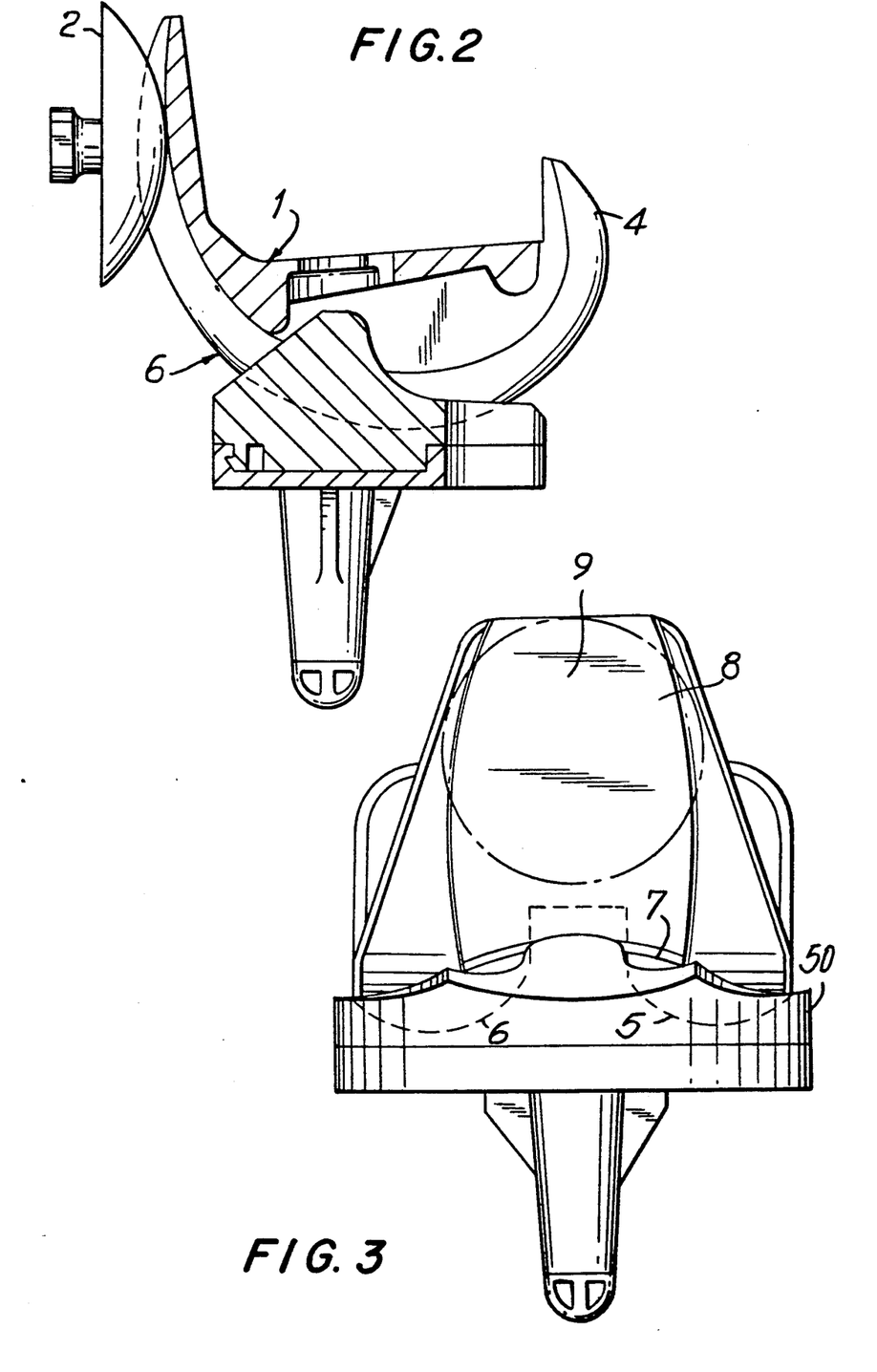
FIG. 2 is a side view of the components of the joint depicted in FIG. 1.
FIG. 3 is a front view of the femoral and tibial components with notation where the patella insert is located.
Figure 5:
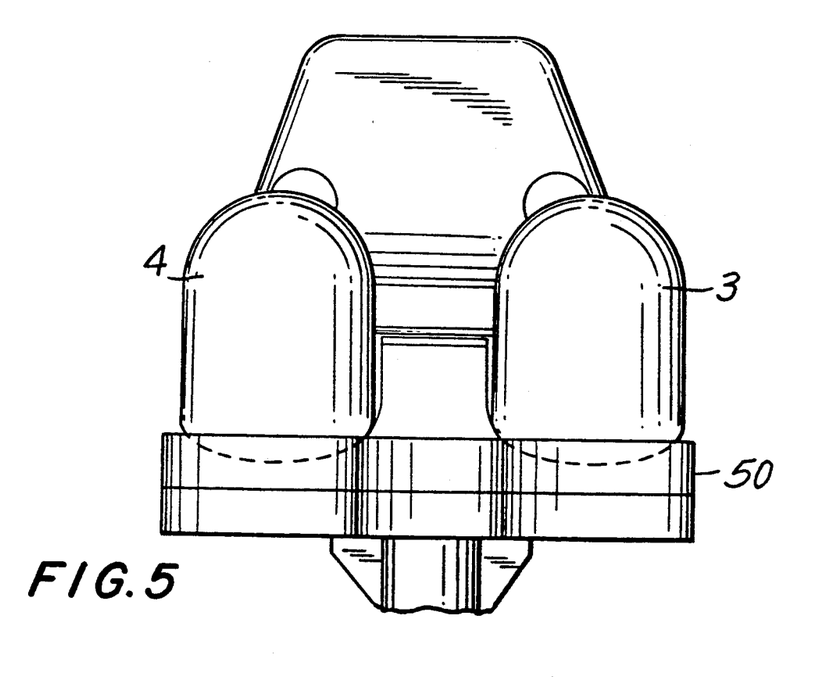
FIG. 5 is a back view of the femoral and tibial components.
Figure 6:
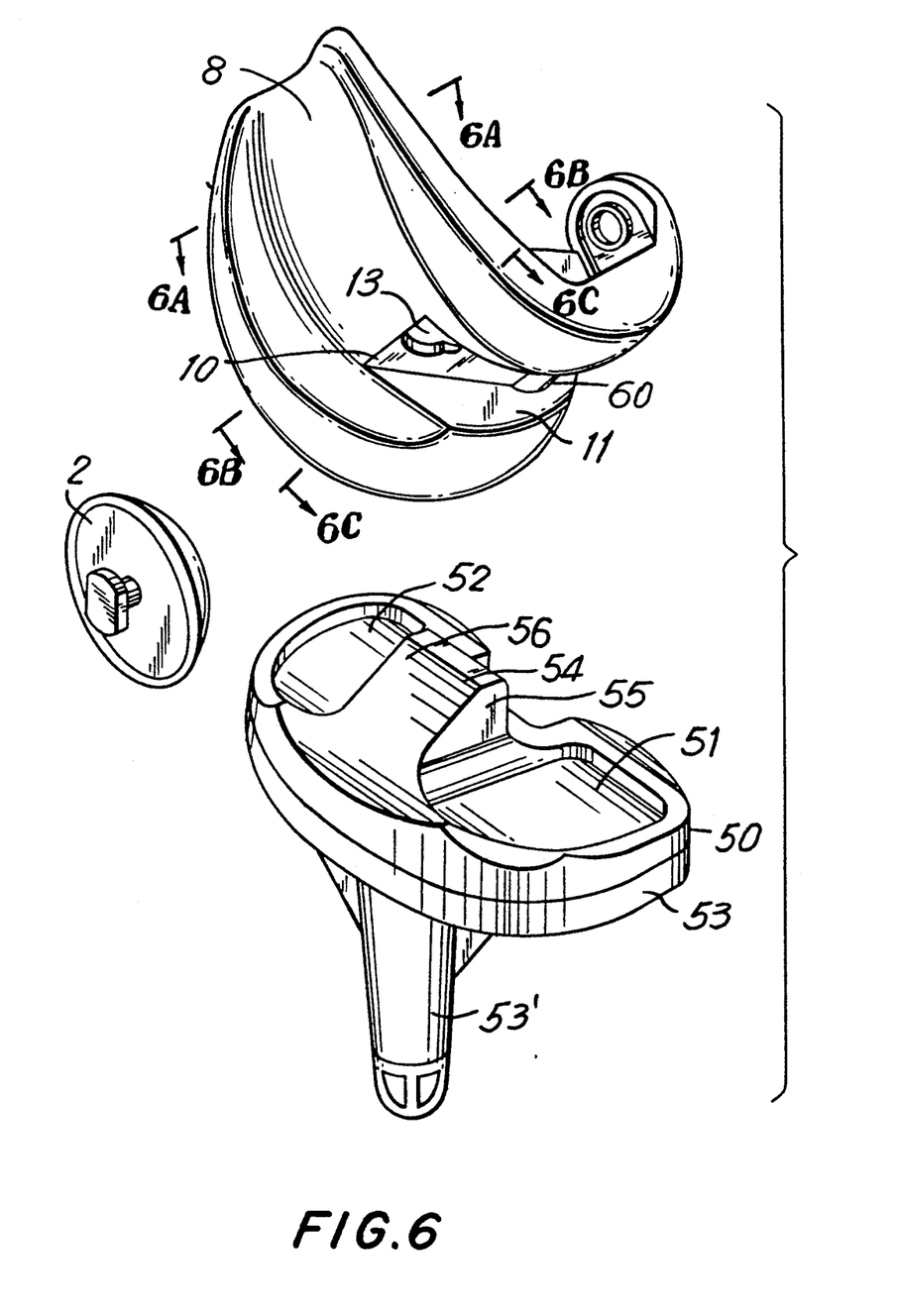
FIG. 6 is an exploded perspective view of the artificial knee joint in accordance with the present invention.
Figure 7:
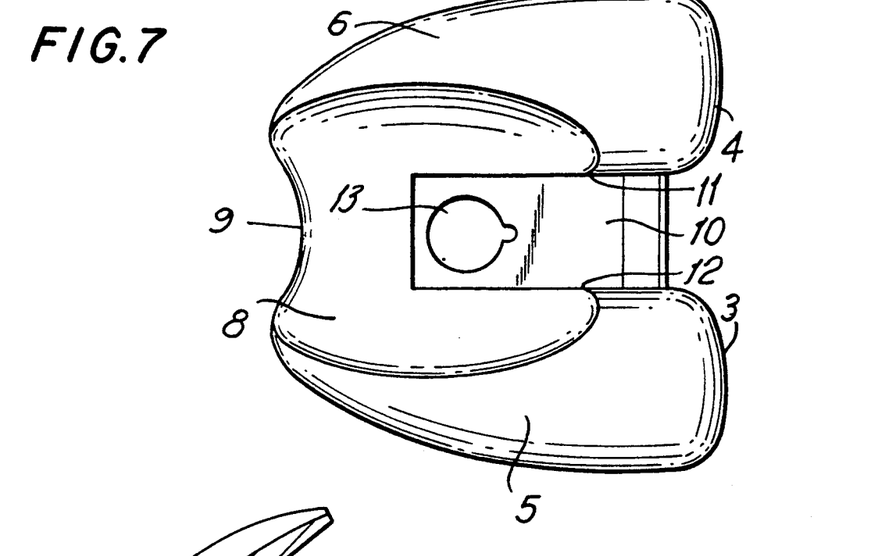
FIG. 7 is a bottom view of the femoral prosthesis component.
Figure 8:
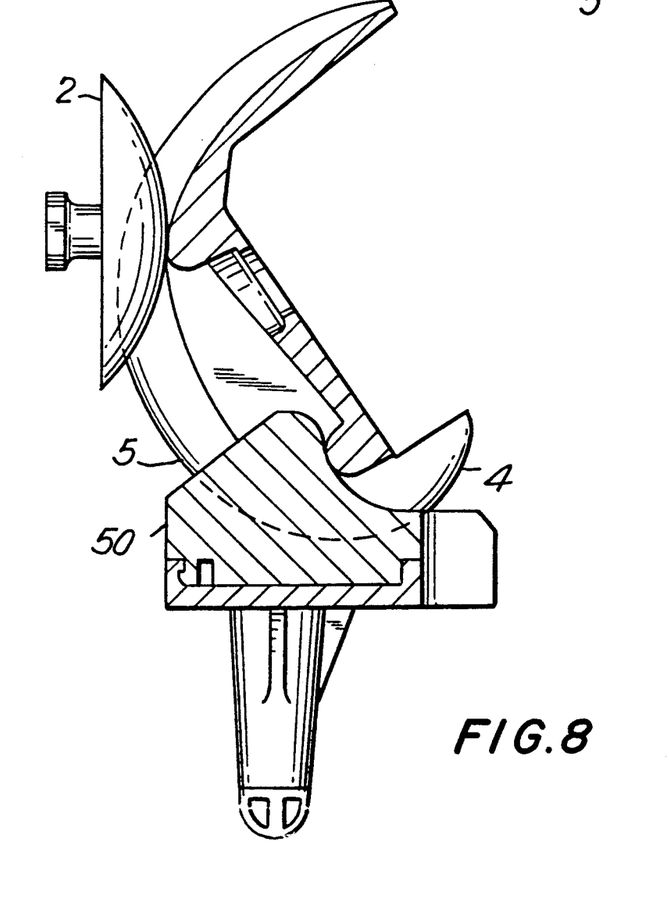
FIG. 8 is a side elevational view of the components of the knee joint in accordance with the present invention.
Figure 9:
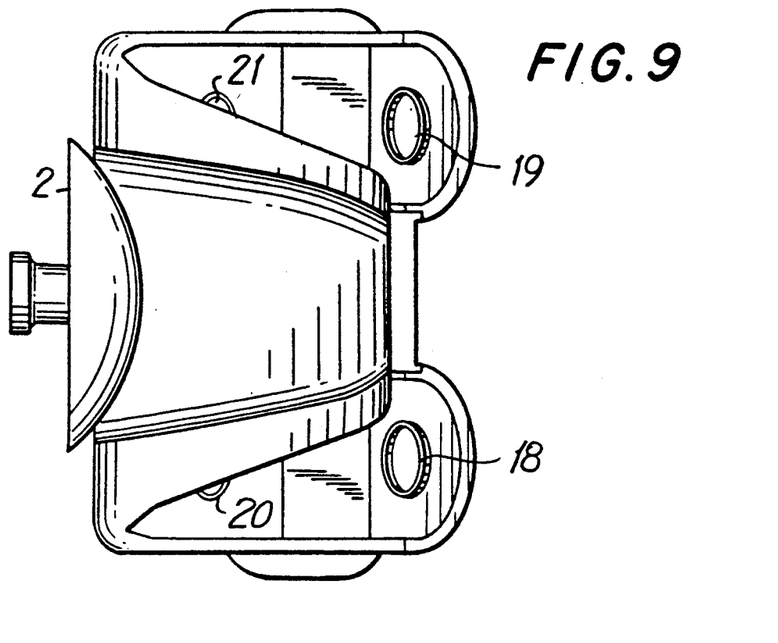
FIG. 9 is a top oblique view of the femoral component with the patellar component in place in the trochlear groove in the femoral component.

Referring to FIGS. 1, 2 and 6, the femoral component 1 comprises a pair of identical laterally spaced-apart femoral condylar portions 3, 4, each of which is smoothly convexly curved in lateral profile generally to match the curvature of an anatomical femoral condyle. Also each portion of 3, 4 is laterally convexly curved as shown in FIGS. 3, 5 and 6 entirely along its anteroposterior extent. The anterior parts of the condylar portions merge smoothly with convexly curved lateral portions, defining a patellar receiving portion 8, having medial part 9. Receiving portion 8 is laterally concave and inferosuperiorly convex according to a predetermined depth-width ratio as depicted in the top view of the femoral component 8 shown in FIG. 4. The patellar portion intersects at its inferior extremity with a superior wall or roof 10 of a box-like intercondylar portion which, together with patellar portion 8 connects the condylar portions 5 and 6. A pair of laterally spaced-apart side walls 11, 12 of the recess join the edges of the roof 10 to the internal edges of the condylar portions.

Figure 4:
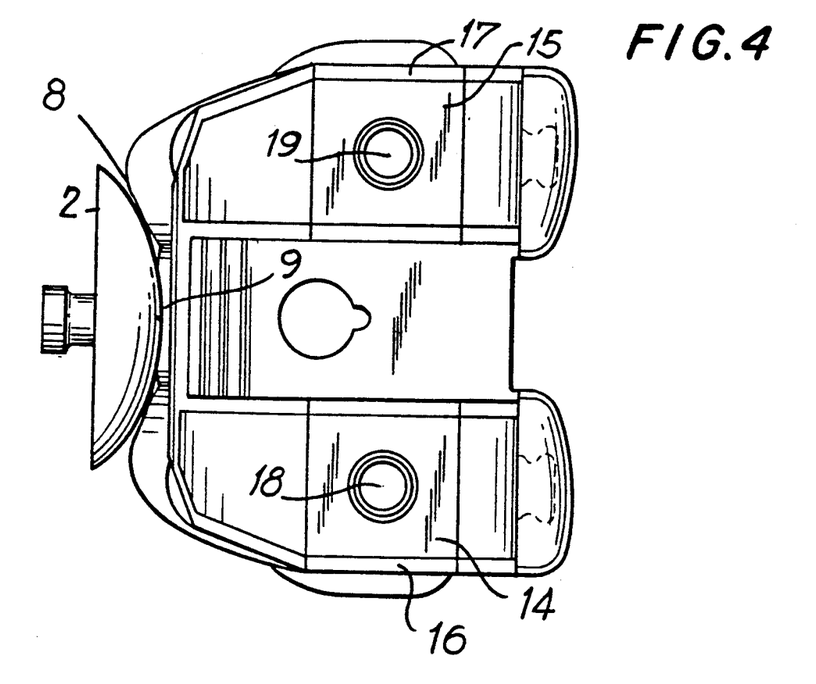
FIG. 4 is a top view of the femoral prosthesis component with the patellar component in place.

The surfaces 14 and 15 in FIG. 4, of the femoral component 1 which face the femur are generally flat and, in the case of the "facets" of each condylar portion are bounded by a small rib or flange 16, 17, thus to provide a keying effect which holds the component securely on the cement used to attach the component to the femur.

The roof 10 of the intercondylar recess is generally flat (though it does have a slight break between two flat surfaces) and, though generally horizontal (parallel to a nominal base plane), slopes posteriorly-superiorly toward a transverse, convex cam follower surface at the posterior extremity. The notches 18, 19, 20 and 21 shown in FIG. 9 on the internal edge of the posterior parts of the condylar portions are there for a purpose relating to the surgical technique and do not have anything to do with the anatomical structure or function of the prosthesis. The femoral component is preferably made of a surgical grade, durable metal, such as a cobalt-chrome-molybdenum alloy meeting ASTM Standard #F75-74. All surfaces which are external to the bone are highly polished. The femoral component is symmetrical about a vertical anteroposterior center plane, so it can be used on either knee.

The tibial component 50 is preferably made of a surgical grade, low-friction, high density, low wearing plastic, such as RCH-1000, and is also symmertrical about a vertical anteroposterior center plane for right or left use. It comprises an oblong, rounded, disc-like plateau portion, the upper surface of which is generally flat and slopes down from front to back. Each of a pair of laterally spaced-apart, oblong concavities 51 and 52 receives one of the femoral condylar portions; the "nested" support of the femoral component stabilizes the prosthetic joint but still permits antero-posterior translation, lateral angulation and rotation, all of which are involved in normal function of the anatomical knee joint. The lateral curvature is slightly greater than the lateral curvature of the femoral condylar portions.

A keel-like fixation post 53' extends from the inferior surface of the plateau portion 53. Cement intrudes into slots on the inferior surface of the plateau portion and anchors the tibial component to the cement.

A stabilizing post 54 extends superiorly from the plateau portion between the concavities 51 and 52 and is received in the femoral intercondylar recess formed by 10, 11 and 12. The post 54 is generally triangular in lateral profile and has flat, parallel lateral surfaces 55 and 56, a concave cam surface at the inferior part of the posterior surface, and an anterior surface which slopes anteriorly and superiorly at an acute included angle to a nominal reference plane perpendicular to the nominal axis of the extended leg. The lateral surfaces of the stabilizing post are in sufficient clearance from the lateral walls of the femoral intercondylar recess formed by roof 10 and side walls 11 and 12 to allow normal lateral angulation and rotation of the prosthetic knee joint.

With the leg extended, a generally stable position is established by nesting of the femoral condyles in the tibial plateau concavities as shown in FIGS. 1, 3, 5 and 8; the tibial stabilizing post and femoral recess do not engage in the antero-posterior direction. Under moderate degrees of flexion, the post 54 and recess formed by 10, 11 and 12 continue to remain functionally dormant, but as flexion increases, there is a greater tendency for the femoral cam follower 60 shown in FIG. 6 to engage the posterior surface of the tibial post if the hamstring muscles of the thigh pull the tibia backward. There is, in such event a tendency to dislocate it posteriorly. Somewhere around 60° to 70° flexion, the femoral cam follower should ordinarily engage the tibial cam surface, and as flexion increases beyond that point the prosthetic femoral condyles will be forced to roll back in the tibial concavities and the zone of contact between the condyles and the concavities shifts posteriorly to a location very close to the posterior extremity of the tibial plateau at full flexion. This shift and the sloping of the tibial plateau allows a high flexion to occur without interference between the posterior extremity of the femur and the posterior extremity of the tibial component. The post 54 and recess formed by 10, 11 and 12 thus stabilize joint functions near and at full flexion by controlling the relative antero-posterior positions of the femur and preventing anterior translation.

In accordance with the novel feature of the present invention, trial prosthesis may be placed and patellar stability checked by flexing the knee. The patella 2 should track in the intercondylar groove 8 of the femoral component 1 without a tendency to sublux or dislocate. If the patella 2 dislocates laterally during this test a lateral retinacular release should be performed.

Patellar tracking is again checked until there is no tendency to sublux or dislocate.

The improvement embodied in the present invention resides inter alia in providing a patellar flange portion extending above the bridging portion joining said condylar bearing portions that has a trochlear groove on the front thereof adapted to receive patellar insert 2 which is affixed posteriorly to the natural patella to form a patellar prosthesis. Varying depth to width ratios of the trochlear groove along its medial axis, when using a patellar prosthesis in place in said groove, provides a means for flexing the leg using less force across the patella because there is less stretching of the ligaments tendons and muscles so strain is reduced compared with prior art prostheses. An angle of flexion can be obtained between about $-8°$ and $120°$ when the interior to posterior dimension of the femoral component is between 50 mm and 70 mm.

Figure 10:
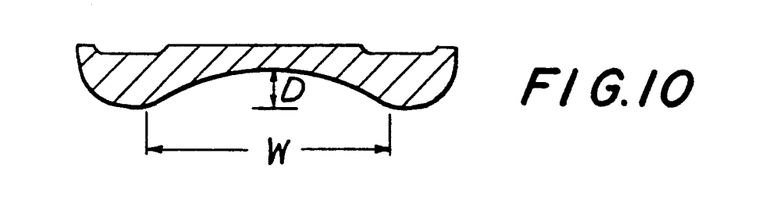
FIGS. 10, 11 and 12 are cross sections taken through the sections noted in FIG. 6A, 6B and 6C showing the depth and width of the grooves at the respective locations.
Figure 11:
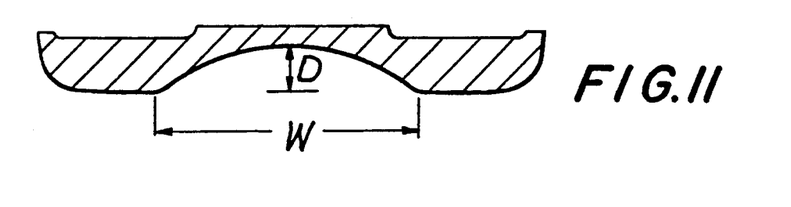
Figure 12:
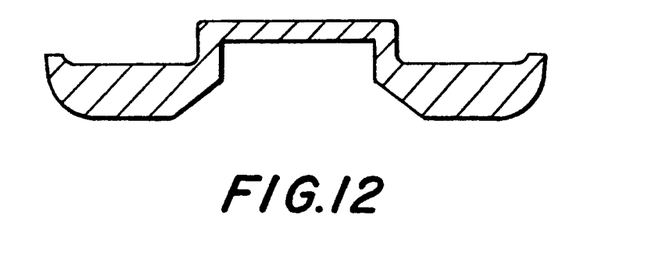

FIGS. 10, 11 and 12 depict cross-sectional views taken through the femoral component at lines A, B and C. FIG. 10 depicts the cross sectional view at 6A showing the depth/width ratio at the anterior/substantially superior portion of the trochlear groove. FIG. 11 depicts the cross-section at 6B at a location inferior to cross-section 6A. This shows greater width and depth dimensions than the dimensions of 6A found in FIG. 10. FIG. 12 depicts the cross-section at FIG. 6C at the highest angle of flexion.

It has been demonstrated that the stress in the patella-femoral joint for any given angle of flexion between $-8°$ and $120°$ in general is remarkably reduced if the depth/width ratio of the trochlear groove found in the femoral component of the knee joint prosthesis is preferably maintained within the range of 0.10 to 0.19. For angles of flexion between 30° and 100°, the depth/width ratio for the various sized femoral components ranges between about 0.14 and 0.19.

A femoral component having a anterior to posterior measurement of a femur that ranges between about 50 mm and 74 mm that has a trochlear groove having a depth to width ratio of between about 0.1 and 0.2 can flex with substantially less strain on the supporting ligaments than heretofor has been possible. It is desireable to keep the radius of curvature which defines the arcs found in FIGS. 10, 11 and 12 based upon the cross sections in FIG. 6 as shallow as possible. As noted in the general description above, as the trochlear groove of the present invention gets wider, it correspondingly gets deeper.

TABLE 1

The anterior to posterior measurement (A/P) of a femur varies from person to person. Four of the most convenient A/P femoral component measurements are 56 mm, 61 mm, 65 mm and 69 mm and are used in the following table. The following table lists the specific values for the flexion angle as a function of depth/width ratio.

DEPTH/WIDTH vs. ANGLE OF FLEXION

| FLEXION ANGLE | Depth/Width Ratio | | | |
|---|---|---|---|---|
| | 56 mm | 61 mm | 65 mm | 69 mm |
| 0 | 0.10 | 0.11 | 0.13 | 0.12 |
| 30 | 0.14 | 0.17 | 0.15 | 0.16 |
| 60 | 0.17 | 0.19 | 0.18 | 0.18 |
| 90 | 0.18 | 0.19 | 0.19 | 0.19 |
| 100 | 0.17 | 0.18 | 0.19 | 0.19 |

The sizes in the table listed above are included by way of illustration and should not be viewed as limiting the scope of the invention. The (A/P) of the femoral component can range from between about 50 mm and 74 mm.

Figure 13:
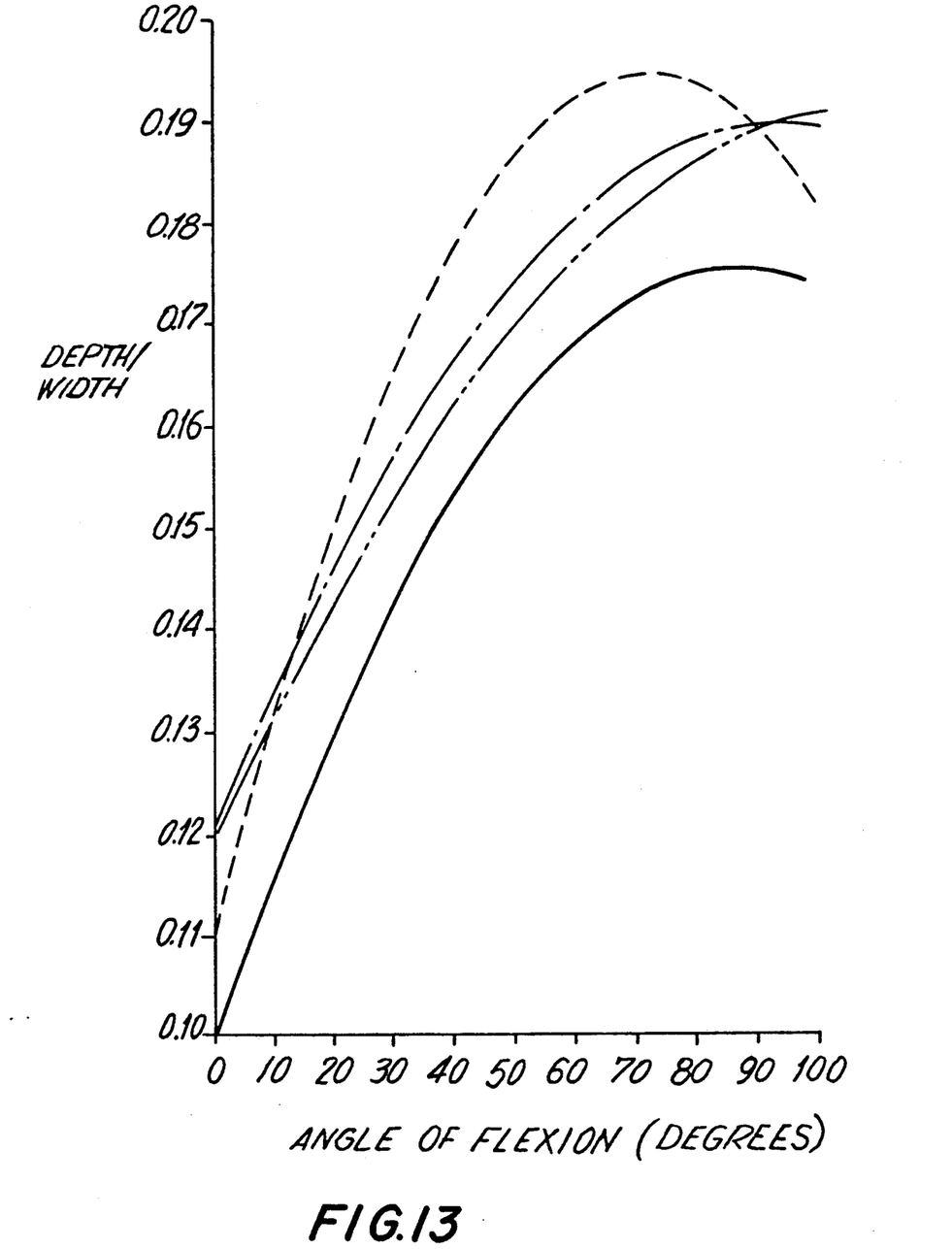
FIG. 13 is a graph depicting the relationship between the depth/width of the trochlear groove and the angle of the flexion of the knee.

FIG. 13 depicts graphically the functional relationship described in Table 1 above.

While the invention has been particularly shown and described with respect to preferred embodiments thereof, it will be understood by those skilled in the art that the foregoing and other changes in form and details may be made therein without departing from the spirit and scope of the invention.

Having thus described my invention, what I claim as new and desire to secure by Letters Patent is:

1. In a knee joint prosthesis having a femoral component which includes a pair of laterally spaced-apart condylar bearing portions, each of which has an external anteroposterior surface which is smoothly convexly curved anteroposteriorly to conform substantially to an anteroposterior surface of a human anatomical femoral condyle, and each of said condylar bearing portions being smoothly convexly curved laterally throughout said anteroposterior surface, configured for mutual articulation with mating portions of a tibial component, and an intercondylar portion joining said two condylar bearing portions;

said prosthesis also having a tibial component which includes a platform having a superior surface containing a pair of laterally spaced-apart concavities, each of which is correspondingly configured to receive in nested relation, one of said condylar portions of said femoral component, and a stabilizing post extending superiorly from said superior surface of said platform intermediate said concavities for reception in the intercondylar portion of the femoral component;

the improvement comprising providing a patellar flange element having an anterior surface extending above the bridging portion joining said condylar bearing portions and having a trochlear groove therein, and having varying depth to width ratios of said groove of between about 0.1 to 0.2 along a medial axis of said trochlear groove configured to receive a patellar insert comprising a patellar prosthesis which when said patellar prosthesis is in place in said trochlear groove, allows an angle of flexion between about $-8°$ and $120°$ when anterior to posterior linear dimensions of the femoral component is within the range of between about 50 mm and about 74 mm, said depth to width ratios being so arranged that said patella rides deeper within said trochlear groove through said angle of flexion than does a patella in a human knee joint.

2. The knee joint prosthesis defined in claim 1 wherein the angle of flexion is between $30°$ and $100°$.

3. The knee joint prosthesis defined in claim 2 wherein said ratios are between about 0.1 and 0.19.

* * * * *